(12) United States Patent
Smith

(10) Patent No.: US 8,795,256 B1
(45) Date of Patent: Aug. 5, 2014

(54) BREAKAWAY VALVE FOR AN IV

(76) Inventor: Jonathan R. Smith, Warsaw, OH (US)

( * ) Notice: Subject to any disclaimer, the term of this patent is extended or adjusted under 35 U.S.C. 154(b) by 587 days.

(21) Appl. No.: 13/085,009

(22) Filed: Apr. 12, 2011

Related U.S. Application Data

(60) Provisional application No. 61/322,924, filed on Apr. 12, 2010.

(51) Int. Cl.
*A61M 25/16* (2006.01)
*A61M 25/18* (2006.01)
*A61M 1/00* (2006.01)
*A61M 5/00* (2006.01)

(52) U.S. Cl.
USPC .............................. 604/537; 604/33; 604/249

(58) Field of Classification Search
CPC ..... A61M 39/00; A61M 39/10; A61M 39/14; A61M 39/26; A61M 2039/0036; A61M 2039/0063; A61M 2039/1027; A61M 2039/1061; A61M 2039/1072; A61M 2039/263; A61M 2039/266; A61M 2039/267; A61M 2039/268; A61M 2039/2473; A61M 2039/2493; F16L 29/00; F16L 29/02; F16L 29/04; F16L 37/28; F16L 37/30; F16L 37/32; F16L 37/36; F16L 37/38; F16L 37/40; F16L 37/42
USPC ................ 604/30, 31, 33, 246, 249, 533–539
See application file for complete search history.

(56) References Cited

U.S. PATENT DOCUMENTS

| 3,921,656 | A |   | 11/1975 | Meisenheimer, Jr. et al. |         |
|-----------|---|---|---------|--------------------------|---------|
| 4,340,049 | A |   | 7/1982  | Munsch                   |         |
| 4,386,622 | A |   | 6/1983  | Munsch                   |         |
| 4,722,725 | A |   | 2/1988  | Sawyer                   |         |
| 4,872,471 | A |   | 10/1989 | Schneider                |         |
| 5,215,538 | A |   | 6/1993  | Larkin                   |         |
| 5,364,371 | A |   | 11/1994 | Kamen                    |         |
| 5,405,339 | A | * | 4/1995  | Kohnen et al.            | 604/535 |
| 5,492,147 | A |   | 2/1996  | Challender et al.        |         |
| 5,820,614 | A | * | 10/1998 | Erskine et al.           | 604/533 |
| 5,848,997 | A | * | 12/1998 | Erskine et al.           | 604/533 |
| 6,146,374 | A | * | 11/2000 | Erskine et al.           | 604/533 |
| 7,153,296 | B2| * | 12/2006 | Mitchell                 | 604/533 |
| 7,959,192 | B2| * | 6/2011  | Elton et al.             | 285/376 |
| 2005/0015075 | A1| * | 1/2005 | Wright et al.           | 604/535 |
| 2005/0101939 | A1| * | 5/2005 | Mitchell                | 604/533 |

* cited by examiner

*Primary Examiner* — Andrew Gilbert
(74) *Attorney, Agent, or Firm* — Robert C. Montgomery; Montgomery Patent & Design

(57) ABSTRACT

A break-away intravenous (IV) therapy fitting designed to eliminate loss of an intravenous site on a patient's arm is herein disclosed, comprising a two-piece coupling having a first side that connects to the IV tubing leading to an IV fluid supply. The second side is connected to the peripheral IV site on the patient's body. In use, the two (2) sides are connected, thereby allowing fluids to flow through. Upon application of a certain amount of stress against the IV tubing, the coupling would detach. Both halves of the coupling comprise internal valving members to avoid leakage, thus stopping flow on either side upon disconnection.

14 Claims, 4 Drawing Sheets

BREAKAWAY VALVE FOR AN IV

RELATED APPLICATIONS

The present invention was first described in and claims the benefit of U.S. Provisional Application No. 61/322,924 filed Apr. 12, 2010, the entire disclosure of which is incorporated herein by reference.

FIELD OF THE INVENTION

The present invention relates generally to intravenous tubes, and in particular, to a breakaway valve for an intravenous tube.

BACKGROUND OF THE INVENTION

Intravenous or IV medicines have greatly enhanced our quality of life. They are very effective, fast acting, easy to administer, and easy to control. Such medicines are typically introduced to the patient via tubing which is connected to an IV needle located in the patient's arm. The needle or tube is held in place with tape, bandages, specialty adhesive covers and the like which form a mostly permanent installation.

A major disadvantage of intravenous setups like those described above is that many patients, who may be in a confused state of mind, are prone to rip out their IV lines. This is dangerous as it leads to medicine being introduced into the room and can cause injury to the patient. Other similar problem is that many patients accidentally remove their IV lines by moving too far from the source of the line.

Various attempts have been made to provide breakaway valves for various fluid lines, including U.S. Pat. No. 3,921,656; U.S. Pat. No. 4,340,049; U.S. Pat. No. 4,722,725; U.S. Pat. No. 4,872,471; U.S. Pat. No. 5,364,371; and U.S. Pat. No. 5,492,147. However, none of these designs are similar to the present invention.

While these devices fulfill their respective, particular objectives, each of these references suffer from one (1) or more of the aforementioned disadvantages. Many such devices are not suitable for use with intravenous tubes. Many such devices do not adequately seal both sides of the valve as is desirable for intravenous tubes. Many such devices do not provide sufficient flow through the valve when operable. Accordingly, there exists a need for a breakaway valve that can be utilized with intravenous tubes without the disadvantages as described above. The development of the present invention substantially departs from the conventional solutions and in doing so fulfills this need.

SUMMARY OF THE INVENTION

In view of the foregoing references, the inventor recognized the aforementioned inherent problems and observed that there is a need for a breakaway valve which provides features specifically suited for medical use. Thus, the object of the present invention is to solve the aforementioned disadvantages and provide for this need.

To achieve the above objectives, it is an object of the present invention to provide connection and disconnection of an intravenous tube at an intermediate point along the tube, particularly in the event of accidental tensioning of the tube while it is in current use delivering a medical fluid to a patient. This prevents loss of the intravenous site, prevents injury to the patient, and prevents loss of fluid. The device includes a first assembly and a second valve assembly which can be coupled together.

Another object of the present invention is to enable connection to a conventional IV kit at an intermediate location using a first IV tube and a second IV tube. The first IV tube is attached to the first valve assembly and to an IV pump or similar fluid supply apparatus. The second IV tube is attached to the second valve assembly and to a peripheral IV site on a patient's body.

Yet still another object of the present invention is to removably attach the first and second valve assemblies by engaging corresponding male and female locking features. The locking features provide a mechanical connection and a sealed liquid connection between the first and second IV tubes.

Yet still another object of the present invention is to comprise the locking features of an interfering and mating annular fit which provides a secure connection between the first and second IV tubes but which can come apart when sufficient tension is applied. The locking features prevent gentle, natural motions such as shifting the patient's arm from disengaging the device, but still allow sudden or sufficient tension to disengage the first and second IV tubes from each other.

Yet still another object of the present invention is for each valve assembly to include a spring-loaded, normally closed valve function that automatically seals the tubes when the locking features are disengaged. Each valve assembly includes a washer attached to a spring that is biased to block a center aperture of the valve assembly and prevent fluid flow.

Yet still another object of the present invention is to further comprise each washer of an actuating feature comprising a hemispherical molded protrusion. When the locking features are engaged, the two (2) actuating features engage each other. The two (2) springs provide an identical force such that the actuating features force each other away an equal amount, exposing the center apertures of each valve assembly and allowing fluid to pass through a plurality of flow apertures space around each washer.

Yet still another object of the present invention is to provide a method of utilizing the device that provides a unique means of installing the device in line with an IV kit, connecting the valve assemblies, enabling fluid flow through the device, automatically separating the valve assemblies under a sufficient amount of tension, automatically isolating the fluid flow within both valve assemblies when the device is disconnected, restoring fluid flow by reconnecting the valve assemblies, and benefiting from a self-sealing IV therapy device which can disconnect without jeopardizing or stressing an intravenous site.

Further objects and advantages of the present invention will become apparent from a consideration of the drawings and ensuing description.

BRIEF DESCRIPTION OF THE DRAWINGS

The advantages and features of the present disclosure will become better understood with reference to the following more detailed description and claims taken in conjunction with the accompanying drawings, in which like elements are identified with like symbols, and in which:

| DESCRIPTIVE KEY | |
|---|---|
| 10 | break-away valve for an IV tube |
| 20 | first valve assembly |
| 22 | first housing |
| 24 | first spring |
| 25 | first washer |
| 26 | first actuator feature |
| 27 | flow aperture |
| 28 | first tube connector |
| 30 | male locking feature |
| 32 | first center aperture |
| 40 | second valve assembly |
| 42 | second housing |
| 44 | second spring |
| 45 | second washer |
| 46 | second actuator feature |
| 48 | second tube connector |
| 50 | female locking feature |
| 52 | second center aperture |
| 60 | first tube |
| 65 | second tube |
| 80 | fluid flow |
| 100 | IV kit |
| 105 | IV site |
| 110 | patient |

DETAILED DESCRIPTION OF THE PREFERRED EMBODIMENT

Figure 1:
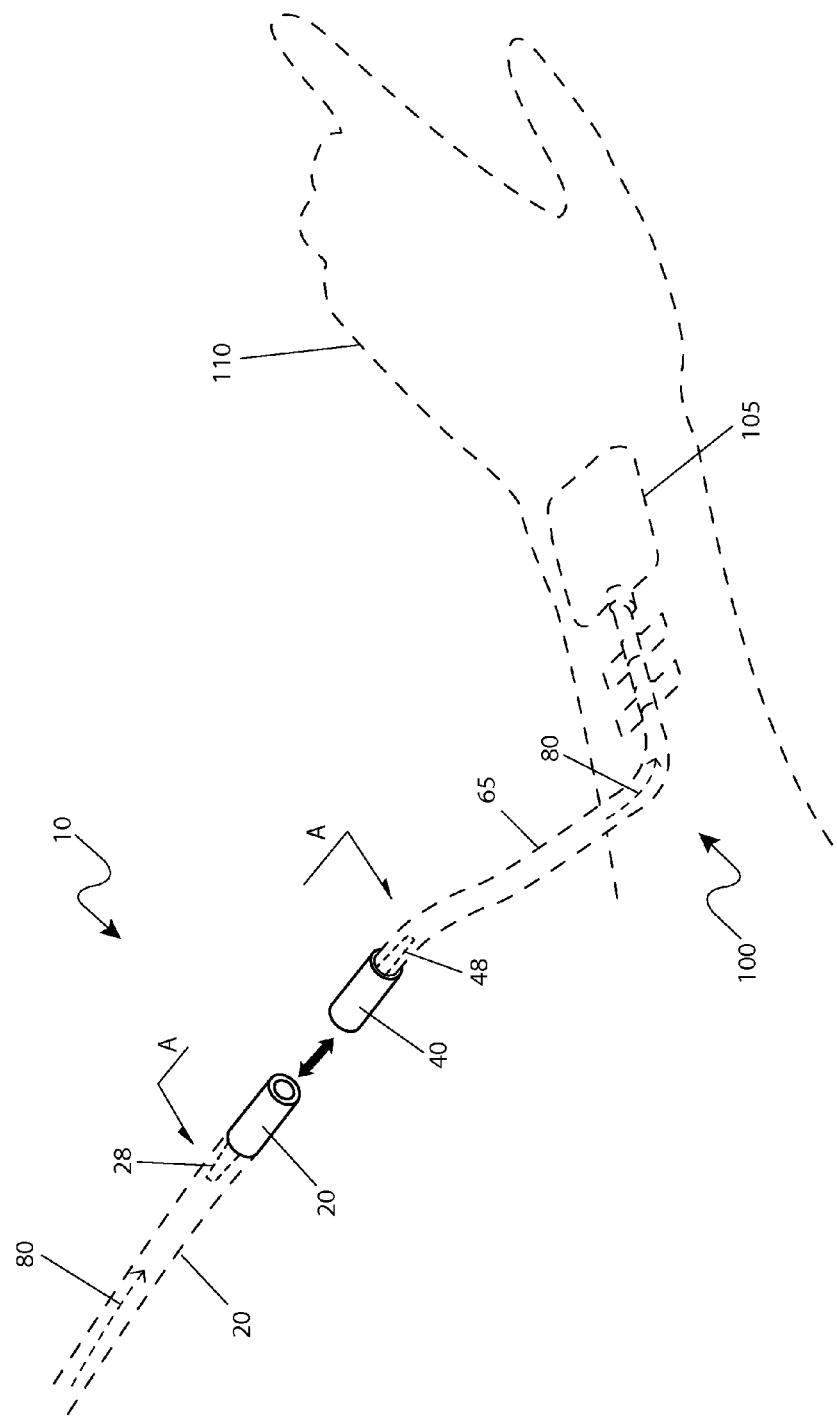
FIG. 1 is a perspective view of a break-away valve for an intravenous (IV) tube 10 depicting an in-use state, according to a preferred embodiment of the present invention.
Figure 2A:
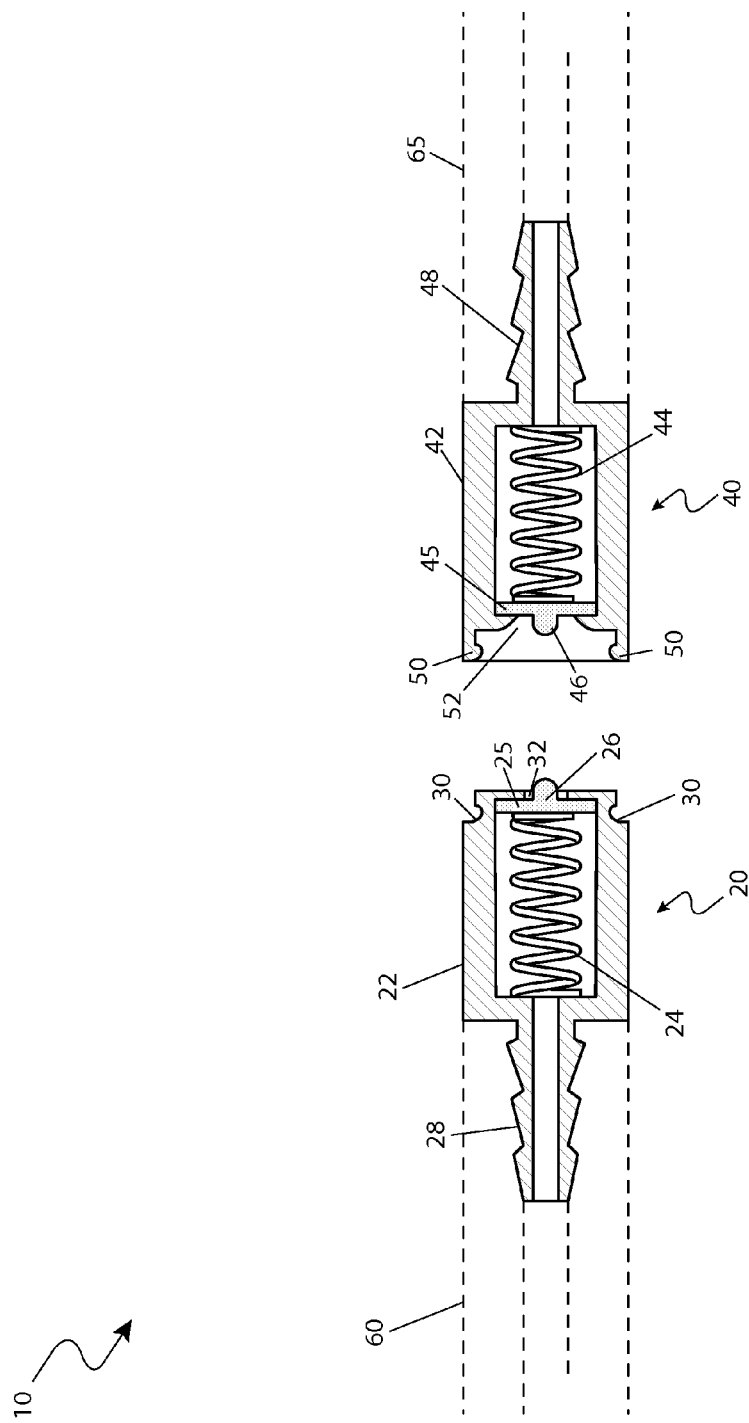
FIG. 2a is a section view of the break-away valve for an IV tube 10 taken along section line A-A (see FIG. 1), depicting a disengaged state, according to a preferred embodiment of the present invention.
Figure 2B:
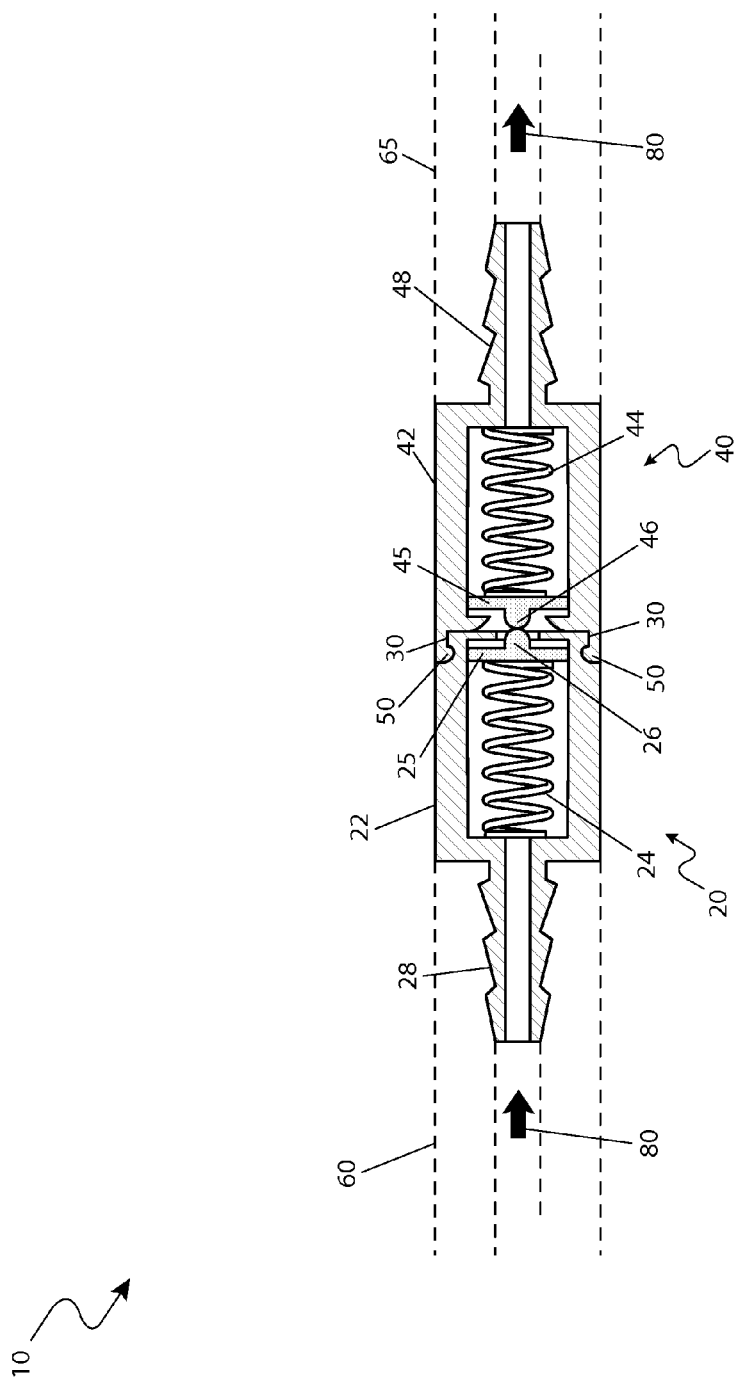
FIG. 2b is a section view of the break-away valve for an IV tube 10 taken along section line A-A (see FIG. 1), depicting an engaged state, according to a preferred embodiment of the present invention; and, FIG. 3 is a close-up view of washer portions 25, 45 of the break-away valve for an intravenous (IV) tube 10, according to a preferred embodiment of the present invention.
Figure 3:
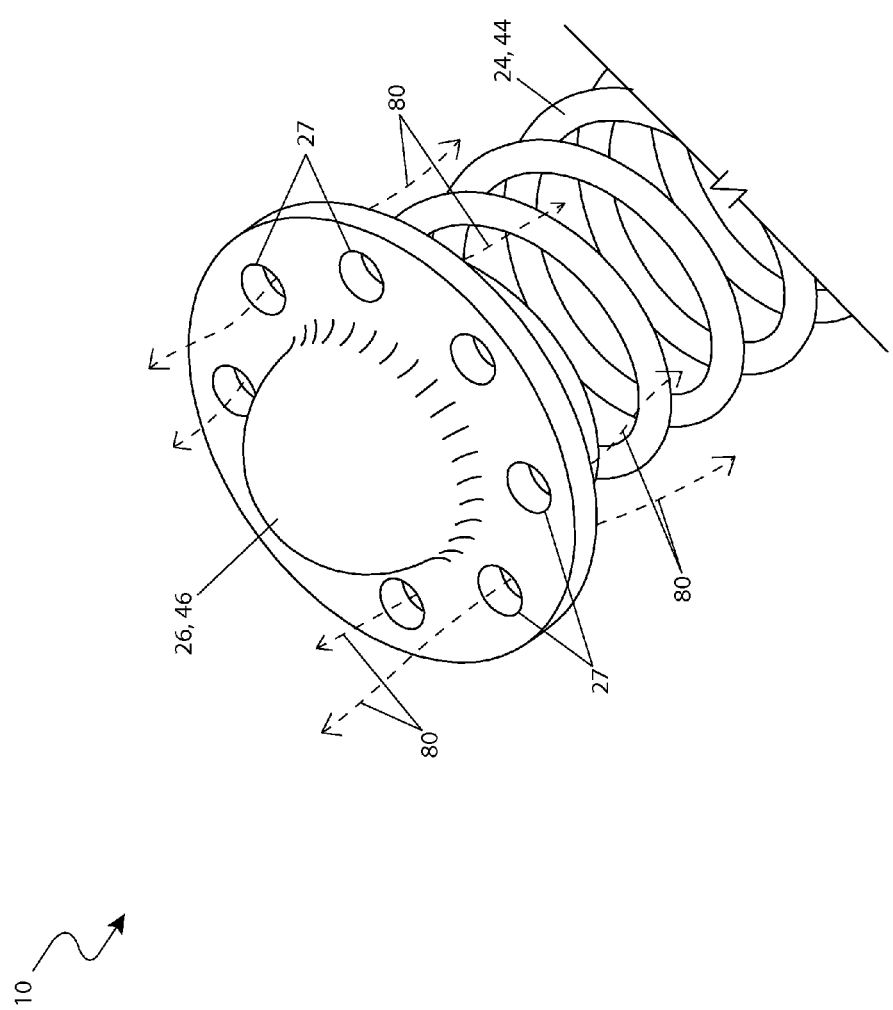

In accordance with the invention, the best mode is presented in terms of a preferred embodiment, herein depicted within FIGS. 1 through 3. However, the disclosure is not limited to a single described embodiment and a person skilled in the art will appreciate that many other embodiments are possible without deviating from the basic concept of the disclosure and that any such work around will also fall under its scope. It is envisioned that other styles and configurations can be easily incorporated into the teachings of the present disclosure, and only one particular configuration may be shown and described for purposes of clarity and disclosure and not by way of limitation of scope.

The terms "a" and "an" herein do not denote a limitation of quantity, but rather denote the presence of at least one of the referenced items.

Referring now to FIG. 1, a perspective view of a break-away valve for an IV tube (herein described as the "device") 10, depicting an in-use state, according to a preferred embodiment of the present invention, is disclosed. The device 10 provides a break-away IV therapy fitting which provides convenient connection/disconnection capability as well as avoiding a loss of an intravenous site 105 on a patient's arm 110 in an event of accidental tensioning of hose portions 60, 65 of the IV kit 100. The device 10 comprises a removably attachable molded plastic coupling and valving device capable of being integrated into hose portions 60, 65 of a conventional IV kit 100 further comprising interlocking first valve assembly 20 and second valve assembly 40 portions. Said first 20 and second 40 valve assemblies comprise internal valving components allowing fluid-tight connection and disconnection, thereby enabling separation of said IV kit 100 at an intermediate position along a tubing portion 60, 65. The first valve assembly 20 is connected to a first IV tube 60 which in turn is envisioned being connected to an IV pump or similar fluid supply equipment. The second valve assembly 40 connects to a second tube 65 envisioned in turn to be connected to a peripheral IV site 105 on a patient's body 110. The first 20 and second 40 valve assemblies are removably attached to each other via a respective male locking feature 30 and a respective female locking feature 50. Engagement of said male 30 and female 50 locking features provides both a mechanical connection and a sealed liquid connection, and a liquid-tight disconnection means upon an event that sufficient tension is applied to the attached tubes 60, 65, thereby allowing the device 10 to snap apart while automatically internally sealing and stopping a fluid flow 80 within both valve assemblies 20, 40.

Referring now to FIGS. 2a and 2b, section views taken along section line A-A (see FIG. 1), depicting respective disengaged and engaged states, according to a preferred embodiment of the present invention, are disclosed. The first valve assembly portion 20 of the device 10 comprises a first valve housing 22, a first spring 24, a first valve washer 25, a first actuator feature 26, a first tube connector 28, and a male locking feature 30. The first valve assembly 20 is in mechanical communication with the second valve assembly 40 being similar in construction and function as the first valve assembly 20, comprising respective second housing 42, second spring 44, second washer 45, second actuator feature 46, second tube connector 48, and female locking feature 50 portions.

The valve assemblies 20, 40 are to be arranged in an "in-line" manner being incorporated into the IV kit 100 envisioned to be located between an IV pump and an IV site 105 upon a patient's 110 wrist or other body area, thereby providing normal delivery of pressurized fluids and fluid medicines in a conventional intravenous manner.

The first 22 and second 42 valve housings comprise hollow cylinder-shaped plastic molded portions comprising the integrally-molded male locking feature 30 and female locking feature 50, respectively, at proximal ends in relation to each other. Said first 22 and second 42 valve housings further comprise respective first tube connector 28 and second tube connector 48 portions at distal ends in relation to each other. In use, the male locking feature 30 is insertingly engaged with the respective and geometrically mated female locking feature 50 via an interfering and mating annular fit, thereby providing a tensile break-away means to safely disconnect the IV supply when pulled apart. Said male locking feature 30 and female locking features 50 further comprise respective first 32 and second 52 center apertures, thereby establishing and maintaining a fluid flow 80 to pass through the device 10 upon connection of the first 20 and second 40 valve assemblies.

Upon disconnection of the device 10, the valve assemblies 20, 40 provide sealed fluid isolation of the first 60 and second 65 tube portions of the IV kit 100 via internal valving portions. The first housing portion 22 of the first valve assembly 20 contains the first spring 24 and the fluid sealing first washer 25, thereby providing a spring-loaded normally-closed valving function during disconnection. In like manner, the second housing portion 42 of the second valve assembly 40 comprises a second spring 44 and a second washer 45 portion. The first 25 and second 45 washer portions comprise synthetic disc-shaped sealing members made using flexible sealing materials such as rubber, latex, or the like. Said first 25 and second 45 washers further comprise respective integrally-molded first 26 and second 46 actuating features which protrude towards each other along a centerline which extends through the device 10. The first 26 and second 46 actuating features are located at proximal end portions of the valve assemblies 20, 40 with respect to each other. The first 26 and second 46 actuating features comprise hemispherical molded protrusions which provide a mechanical interference with each other upon engagement of the valve assemblies 20, 40, thereby subsequently compressing the springs 24, 44 and unseating the washers 25, 45 from respective center apertures 32, 52, allowing a fluid flow 80 to pass through flow apertures 27 and through the device 10 (see FIG. 3).

The tube connectors 28, 48 provide a tubing connection means to existing first 60 and second 65 fluid tubing portions of the IV kit 100. Said tube connectors 28, 48 are depicted here comprising molded male barbed fixtures, thereby providing common press-on tubing attachment; however, various other attachment means may be provided in conjunction with or instead of the barbed connectors 28, 48 such as crimp-collars, hose clamps, adhesive bonding, plastic welding, and the like, without deviating from the concept and as such should not be interpreted as a limiting factor of the device 10.

Referring now to FIG. 3, a close-up view of washer portions 25, 45 of the device 10, according to a preferred embodiment of the present invention, is disclosed. The valve assemblies 20, 40 comprise respective washer portions 25, 45 being under spring 24, 44 pressure, thereby sealing against respective first 32 and second 52 center aperture portions which provide a valve seat function (see FIGS. 2a and 2b). Said washer portions 25, 45 further comprise a plurality of flow apertures 27 being formed through a thickness of said washers 25, 45 and radially spaced, thereby allowing the fluid flow 80 to pass through. The washers 25, 45 provide a mechanical interference of respective actuator features 26, 46 upon engagement of the valve assemblies 20, 40, thereby enabling the fluid flow 80 to pass through the device 10 as previously described.

It is envisioned that other styles and configurations of the present invention can be easily incorporated into the teachings of the present invention, and only one particular configuration shall be shown and described for purposes of clarity and disclosure and not by way of limitation of scope.

The preferred embodiment of the present invention can be utilized by the common user in a simple and effortless manner with little or no training. After initial purchase or acquisition of the device 10, it would be installed as indicated in FIG. 1.

The method of utilizing the device 10 may be achieved by performing the following steps: pressing the first tube connector portion 28 of the first valve assembly 20 into the first tube portion 60 of an IV kit 100, envisioned to be connected to a fluid pump or other fluid supply equipment; pressing the second tube connector portion 48 of the second valve assembly 40 into the second tube portion 65, further envisioned to be affixed to an IV needle portion of said IV kit 100; using portions of said IV kit 100 to establish an IV site 105 upon a patient's 110 wrist or other body area in a conventional manner; connecting the first 20 and second 40 valve assemblies together, if not previously joined, by manually engaging the male locking feature 30 and the female locking feature 50 until said features 30, 50 provide a positive snapping insertion; allowing a fluid flow 80 to commence through the device 10 for a period of time, as needed; allowing said first 20 and second 40 valve assemblies to separate upon receiving a sufficient amount of exerted tension upon the tube portions 60, 65 due to actions such as, but not limited to, a confused patient, tangling around an obstruction, intentional disconnection by a care giver, or the like; disconnecting said valve assemblies 20, 40 to automatically seal the washers 25, 45 and isolate the fluid flow 80 within both valve assemblies 20, 40; restoring a fluid flow 80 through the device 10 by connecting the first 20 and second 40 valve assemblies together allowing the fluid flow 80 to commence; and, benefiting from an in-line self-sealing IV therapy device 10 which provides sealed connect/disconnect capability without jeopardizing or stressing an intravenous site 105.

The foregoing descriptions of specific embodiments have been presented for purposes of illustration and description. They are not intended to be exhaustive or to limit the invention and method of use to the precise forms disclosed. Various modifications and variations can be appreciated by one skilled in the art in light of the above teachings. The embodiments have been chosen and described in order to best explain the principles and practical application in accordance with the invention to enable those skilled in the art to best utilize the various embodiments with expected modifications as are suited to the particular use contemplated. It is understood that various omissions or substitutions of equivalents are contemplated as circumstance may suggest or render expedient, but is intended to cover the application or implementation without departing from the spirit or scope of the claims of the invention.

What is claimed is:

1. A connection for intravenous therapy, including:
   a first valve assembly in fluid communication with a first IV tube in fluid communication with a fluid supply equipment, further comprising:
   a first valve housing, comprising a hollow cylinder-shaped body comprising a male locking feature at a proximal end thereof;
   a first tube connector outwardly extending from a distal end thereof;
   a first center proximal aperture located at said proximal end;
   a first center distal aperture located at said distal end;
   a first fluid tube in fluid communication between said first center proximal aperture and said first center distal aperture; and,
   a first positive seal located within said first fluid tube, wherein said first positive seal is biased against said first center proximal aperture to seal to said first valve assembly, said first positive seal further comprising:
   a first spring, having a first end affixed to an interior of said first fluid tube;
   a first washer, having a first side connected to a second end of said first spring, further comprising a first actuating feature centrally located on a second side and outwardly protruding therefrom; and,
   a plurality of first flow apertures formed through said first washer and radially spaced;
   wherein said first spring biases said first washer against said first center proximal aperture, such that said first washer fully engages said first center proximal aperture; and,
   wherein said first washer comprises a flexible sealing material;
   a second valve assembly in fluid communication with a second IV tube in fluid communication with a peripheral IV site;
   wherein said male locking feature is mechanically removably interconnected with a female locking feature located on said second valve assembly;
   wherein said first valve assembly is removably interconnected with said second valve assembly, thereby providing a mechanical and a fluid communication with a fluid seal between said fluid supply equipment and said peripheral IV site;

wherein said first positive seal seals said fluid supply equipment and said first valve assembly during a breakaway event between said first valve assembly and said second valve assembly;

wherein said first positive seal is released when said first valve assembly and said second valve assembly are interconnected, thereby permitting passage of fluid through said first valve assembly;

wherein said second valve assembly provides a second positive seal for said peripheral IV site during a breakaway event between said first valve assembly and said second valve assembly; and, wherein said second valve assembly operably forces said first actuating feature to compress said first spring, thereby unseating said first washer and enabling passage of fluid through said plurality of first flow apertures when said first valve assembly is connected to said second valve assembly.

2. The connection of claim 1, wherein said first tube connector further comprises a molded barbed fixture integral with said first valve housing distal end.

3. The connection of claim 1, wherein said first actuating feature further comprises a hemispherical protrusion integrally molded into said first washer.

4. The connection of claim 1, wherein said second valve assembly further comprises:
a second valve housing, comprising a hollow cylinder-shaped body comprising said female locking feature at a proximal end thereof;
a second tube connector outwardly extending from a distal end thereof;
a second center proximal aperture located at said proximal end;
a second center distal aperture located at said distal end;
a second fluid tube in fluid communication between said second center proximal aperture and said second center distal aperture; and,
said second positive seal located within said second fluid tube;
wherein said second positive seal is biased against said second center proximal aperture to seal to said second valve assembly;
wherein said second positive seal is released when said first valve assembly and said second valve assembly are interconnected, thereby permitting passage of fluid through said second valve assembly.

5. The connection of claim 4, wherein said second tube connector further comprises a molded barbed fixture integral with said second valve housing distal end.

6. The connection of claim 4, wherein said second positive seal further comprises:
a second spring, having a first end affixed to an interior of said second fluid tube;
a second washer, having a first side connected to a second end of said second spring, further comprising a second actuating feature centrally located on a second side and outwardly protruding therefrom; and,
a plurality of second flow apertures formed through said second washer and radially spaced;
wherein said second spring biases said second washer against said second center proximal aperture, such that said second washer fully engages said second center proximal aperture;

wherein said first valve assembly operably forces said second actuating feature to compress said second spring, thereby unseating said second washer and enabling passage of fluid through said plurality of second flow apertures when said first valve assembly is connected to said second valve assembly; and, wherein said second washer comprises a flexible sealing material.

7. The connection of claim 6, wherein said second actuating feature further comprises a hemispherical protrusion integrally molded into said second washer.

8. A connection for intravenous therapy, including:
a first IV tube having a first end in fluid communication with a fluid supply equipment;
a first valve assembly in fluid communication with a second end of said first IV tube, further comprising:
a first valve housing, comprising a hollow cylinder-shaped body comprising said male locking feature at a proximal end thereof;
a first tube connector outwardly extending from a distal end thereof;
a first center proximal aperture located at said proximal end;
a first center distal aperture located at said distal end;
a first fluid tube in fluid communication between said first center proximal aperture and said first center distal aperture; and,
a first positive seal located within said first fluid tube, wherein said first positive seal is biased against said first center proximal aperture to seal to said first valve assembly, said first positive seal further comprising:
a first spring, having a first end affixed to an interior of said first fluid tube;
a first washer, having a first side connected to a second end of said first spring, further comprising a first actuating feature centrally located on a second side and outwardly protruding therefrom; and,
a plurality of first flow apertures formed through said first washer and radially spaced;
wherein said first spring biases said first washer against said first center proximal aperture, such that said first washer fully engages said first center proximal aperture; and,
wherein said first washer comprises a flexible sealing material;
a second IV tube having a first end in fluid communication with a peripheral IV site;
a second valve assembly in fluid communication with a second end of said second IV tube;
wherein said male locking feature located on said first valve assembly is mechanically removably interconnected with a female locking feature located on said second valve assembly;
wherein said first valve assembly is removably interconnected with said second valve assembly, thereby providing a mechanical and a fluid communication with a fluid seal between said fluid supply equipment and said peripheral IV site;
wherein said first positive seal seals said fluid supply equipment and said first valve assembly during a breakaway event between said first valve assembly and said second valve assembly;
wherein said first positive seal is released when said first valve assembly and said second valve assembly are interconnected, thereby permitting passage of fluid through said first valve assembly;

wherein said second valve assembly provides a second positive seal for said peripheral IV site during a breakaway event between said first valve assembly and said second valve assembly; and, wherein said second valve assembly operably forces said first actuating feature to compress said first spring, thereby unseating said first washer and enabling passage of fluid through said plurality of first flow apertures when said first valve assembly is connected to said second valve assembly.

9. The connection of claim 8, wherein said first tube connector further comprises a molded barbed fixture integral with said first valve housing distal end.

10. The connection of claim 8, wherein said first actuating feature further comprises a hemispherical protrusion integrally molded into said first washer.

11. The connection of claim 8, wherein said second valve assembly further comprises:
- a second valve housing, comprising a hollow cylinder-shaped body comprising said female locking feature at a proximal end thereof;
- a second tube connector outwardly extending from a distal end thereof;
- a second center proximal aperture located at said proximal end;
- a second center distal aperture located at said distal end;
- a second fluid tube in fluid communication between said second center proximal aperture and said second center distal aperture; and,
- said second positive seal located within said second fluid tube;
- wherein said second positive seal is biased against said second center proximal aperture to seal to said second valve assembly;
- wherein said second positive seal is released when said first valve assembly and said second valve assembly are interconnected, thereby permitting passage of fluid through said second valve assembly.

12. The connection of claim 11, wherein said second tube connector further comprises a molded barbed fixture integral with said second valve housing distal end.

13. The connection of claim 11, wherein said second positive seal further comprises:
- a second spring, having a first end affixed to an interior of said second fluid tube;
- a second washer, having a first side connected to a second end of said second spring, further comprising a second actuating feature centrally located on a second side and outwardly protruding therefrom; and,
- a plurality of second flow apertures formed through said second washer and radially spaced;
- wherein said second spring biases said second washer against said second center proximal aperture, such that said second washer fully engages said second center proximal aperture;
- wherein said first valve assembly operably forces said second actuating feature to compress said second spring, thereby unseating said second washer and enabling passage of fluid through said plurality of second flow apertures when said first valve assembly is connected to said second valve assembly; and,
- wherein said second washer comprises a flexible sealing material.

14. The connection of claim 13, wherein said second actuating feature further comprises a hemispherical protrusion integrally molded into said second washer.

\* \* \* \* \*